United States Patent
Golinski et al.

(10) Patent No.: US 6,224,637 B1
(45) Date of Patent: May 1, 2001

(54) COMPOSITION FOR THE DYEING OF HUMAN HAIR

(75) Inventors: Frank Golinski, Darmstadt; Heribert Lorenz, Grioss-Bieberau; Helmar Rudolf Wagner, Darmstadt, all of (DE)

(73) Assignee: Goldwell GmbH (DE)

( * ) Notice: Subject to any disclaimer, the term of this patent is extended or adjusted under 35 U.S.C. 154(b) by 0 days.

(21) Appl. No.: 09/324,480

(22) Filed: Jun. 2, 1999

(30) Foreign Application Priority Data

Jun. 25, 1998 (DE) .............................................. 198 28 205

(51) Int. Cl.$^7$ ....................................................... A61K 7/13
(52) U.S. Cl. ........................... 8/412; 8/408; 8/409; 8/411; 8/416; 8/421
(58) Field of Search ................................ 8/408, 409, 410, 8/411, 412, 416, 421

(56) References Cited

U.S. PATENT DOCUMENTS 4,840,639 * 6/1989 Husemeyer et al. ...................... 8/410

FOREIGN PATENT DOCUMENTS

| 3145141 | * | 5/1983 | (DE) . |
| 19614303 | * | 10/1997 | (DE) . |
| 19807245 | * | 2/1999 | (DE) . |
| 2239265 | * | 6/1991 | (GB) . |
| 98/52519 | * | 11/1998 | (WO) . |
| 98/52523 | * | 11/1998 | (WO) . |

OTHER PUBLICATIONS

Caplus Abstract of JP 10–324,618, Kao Corp., Dec. 1998.*

* cited by examiner

Primary Examiner—Caroline D. Liott
(74) Attorney, Agent, or Firm—Norris, McLaughlin & Marcus P.A.

(57) ABSTRACT

A hair dyeing composition achieving intensive, stable colorations, which can be varied by the addition of further coupling substances, contains an oxidation dyestuff system reacting with peroxide comprising a combination of a) 2-(2,5-diaminophenyl)ethanol of the water-soluble salts thereof, and
b) 2,6-dichloro-4-aminophenol.

4 Claims, No Drawings

COMPOSITION FOR THE DYEING OF HUMAN HAIR

BACKGROUND OF THE INVENTION

The present invention concerns a composition for the coloration of human hair on the basis of an oxidation-dyestuff system reacting with peroxide, providing intensive, permanent colors used either as such, or which can, in combination with further developing and/or coupling substances, be used to achieve additional variations.

The developing substances still used most frequently in hair dyeing compositions are 1,4-diaminobenzene (p-phenylenediamine) and 1-methyl-2,5diaminobenzene (p-toluylenediamine). Use of these substances still may entail problems to the extent that in special cases they can lead to skin sensitization in extremely sensitive persons (so-called "para-allergies").

It has already been attempted to solve this problem by the use of alternative developing substances. To a limited extent, this is possible by the use of tetraaminopyrimidine; however it is then necessary to accept diminished color intensity and reduced possibilities to vary the different shades.

A further solution of the problem, namely the virtual absence of a skin sensitizing effect on one hand and an enhanced level of variations in the preparation of possible shades on the other hand, is achieved by the use of 2-(2'-hydroxyethyl amino)-5-aminotoluene or the water-soluble salts thereof, described in EP-A 615 743, and incorporation of triaminohydroxy pyrimidines, in particular 2,5,6-triamino-4-hydroxy pyrimidine, 2,4,5-triamino-6-hydroxy pyrimidine, 4,5,6-triamino-2-hydroxy pyrimidine or the salts thereof, in particular the sulfates, disclosed in EB 467 026 as developing substances in hair dyeing compositions. Even these changes leave room for improvement with regard to coloration. DE-A 196 14 303 therefore discloses oxidation dyestuff substances containing 2-(2'-hydroxyethyl amino)-5-toluene or the salts thereof as developing substances in combination with 2,6-dichloro-4-aminophenol.

Although this combination permits achievement of a multitude of different shades, the degree of variation as well as color intensity can still be optimized.

SUMMARY OF THE INVENTION

It has now been found that an intensive hair coloration which is stable against the influence of light, repeated shampooing and permanent waving without irritating or sensitizing the skin can be obtained, if an oxidation dyestuff system reacting with peroxide is used which comprises a combination of 2-(2,5-diaminophenyl)ethanol or the water-soluble salts thereof, and 2,6-dichloro4-aminophenol.

Application of these compositions on the basis of a customary carrier achieves very expressive, intensive, long-lasting hair colorations after oxidation with peroxide, which can be varied to achieve additional shades by the addition of additional coupling and developing substances.

DESCRIPTION OF THE PREFERRED EMBODIMENT

Such preferred substances are selected in particular from the group encompassing 1-methoxy-2-amino-4-(β-hydroxyethyl amino)benzene, 2-amino-3-hydroxypyridine, 2,6-diaminopyridine, 3-amino-2-methyl amino-6-methoxypyridine, 2-(dimethyl amino)-5-aminopyridine, 1-(β-hydroxyethyl)-2,5-diaminobenzene, 2-(2'-hydroxyethyl amino)-5-aminotoluene, 2,5,6-triamino-4-hydroxypyrimidine, 5-amino-2-methyl phenol, 4-amino-3-methyl phenol, 2,5-diaminopyridine, 2-amino-5-N,N-diethyl aminotoluene, 1,4-diaminobenzene, 2,5-diaminotoluene, 1,3-diaminobenzene, 1-methyl-2-hydroxy-4-aminobenzene, resorcinol, 2-methyl resorcinol, 4-chlororesorcinol, 1-naphthol, 2-aminophenol, 3-aminophenol, 5-amino-2-methoxy phenol, and/or 2-amnino-4-(β-hydroxyethyl amino)anisole or the water-soluble salts thereof.

The use of 2-(2,5-diaminophenyl)-ethanol as developing substance in hair dyeing compositions has already been disclosed in EP-A 7537 and EP-B 400 330, however, the effects achieved with the combinations according to the invention cannot be obtained with the systems described therein.

Use of further developing substances known per se is also possible. In addition to those named above, reference is made in particular to 4-aminophenol, 5-amino salicylic acid and/or 1,2,4-triaminobenzene.

The total concentration of developing substances customarily ranges between about 0.05% and 5%, preferably 0.1% and 4%, in particular 0.25% to 0.5% and 2.5% to 3% by weight, calculated to total hair dyeing composition (excluding the oxidation agent), whereby these figures always refer to the proportion of free base.

The weight proportion of 2-(2,5-diaminophenyl)ethanol to 2,6-dichloro-4-aminophenol ranges between about 1:8 to 8:1, preferably about 1:5 to 5:1, in particular 1:2 to 2:1.

In the hair dyeing compositions according to the invention, the coupling substances as reaction partners of the developing substance(s) have about the same molecular proportion as the developing substances, i.e., in amounts from 0.05% to 5.0%, preferably 0.1% to 4%, in particular 0.5% to 3% by weight, calculated to the total composition (excluding the oxidation agent), whereby these figures always refer to the proportion of free base.

If desired, the compositions according to the invention may also contain so-called shading agents for precise adjustment of the desired shade, in particular direct-acting dyestuffs.

Such shading agents are, for example, nitro dyestuffs such as 2-amino-4,6-dinitrophenol, 2-amino-4-nitrophenol, 2-amino-6-chloro-4-nitrophenol, etc., preferably in amounts from about 0.05% to 2.5%, in particular 0.1% to 1% by weight of the dyestuff composition (excluding the oxidizing agent).

The hair dyeing compositions according to the invention can also comprise the basic substances and additives customarily found in such compositions, i.e. conditioners, etc., known as state of the art and described, for example, in the monography of K. Schrader, "Grundlagen and Rezepturen der Kosmetika", 2nd Ed. (Hüthig Buch Verlag, Heidelberg, 1989), pp. 782 to 815.

They can be prepared as solutions, creams, gels or also in form of aerosol products; suitable carrier compositions are well known.

For application, the oxidation dyestuff precursor is mixed with an oxidizing agent. Preferred oxidizing agent is hydrogen peroxide, for example in concentrations from 2% to 6%. However, it is also possible to use other peroxides, such as urea peroxide and melamine peroxide.

The pH-value of the ready-to-use hair-dyeing composition, i.e. after admixture with peroxide, can be in the slightly acidic range, i.e. from 5.5 to 6.9, as well as in the neutral and in the alkaline range, i.e. between pH 7.1 and 9.5.

Following are various Examples of embodiments illustrating the invention.

| Carrier Composition | |
|---|---|
| Stearyl alcohol | 8.0 (% by wt.) |
| Coco fatty acid monoethanolamide | 4.5 |
| 1.2-Propanedial mono/disterate | 1.3 |
| Coco fatty alcohol polyglycol ether | 4.0 |
| Sodium laury sulfate | 1.0 |
| Oleic acid | 2.0 |
| 1.2-Propanediol | 1.5 |
| Na-EDTA | 0.5 |
| Sodium sulfite | 1.0 |
| Protein hydrolyzate | 0.5 |
| Ascorbic acid | 0.2 |
| Perfume | 0.4 |
| Ammonia, 25% | 1.0 |
| Ammonium chloride | 0.5 |
| Panthenol | 0.8 |
| Water | ad 100.0 |

The oxidation dyestuff combinations according to the invention were incorporated into this carrier base, whereby the water content was reduced accordingly.

The colorations were effected on wool patches and strands of bleached human hair by application of a 1:1 mixture of the dyestuff precursor and 6% hydrogen peroxide solution and twenty minutes processing at room temperature with subsequent washing and drying.

The following colorations were obtained:

EXAMPLE 1

| 0.28 (% by wt.) | 2-(2.5-Diaminophenyl)ethanol sulfate (A 80) |
|---|---|
| 0.20 | 2.6-Dichloro-4-aminophenol |
| 0.25 | 3-Aminophenol |
| Coloration: Intensive dark violet. | |

EXAMPLE 2

| 0.28 (% by wt.) | SA 80 |
|---|---|
| 0.20 | 2,6-Dichloro-4-aminophenol |
| 0.32 | α-Naphthol |
| Coloration: Intensive, expressive azure blue. | |

EXAMPLE 3

| 0.28 (% by wt.) | A 80 |
|---|---|
| 0.20 | 2,6-Dichloro-4-aminophenol |
| 0.28 | 1-Methyl-2-hydroxy-4-aminobenzene |
| Coloration: Intensive, glossy violet. | |

EXAMPLE 4

| 0.28 (% by wt.) | A 80 |
|---|---|
| 0.20 | 2,6-Dichloro-4-aminophenol |
| 0.28 | 2-Methyl resorcinol |
| Coloration: Intensive, glossy olive-brown. | |

EXAMPLE 5

| 0.28 (% by wt.) | A 80 |
|---|---|
| 0.20 | 2.6-Dichloro-4-aminophenol |
| 0.25 | 2-Amino-3-hydroxypridine |
| Coloration: Glossy red-brown. | |

EXAMPLE 6

| 0.28 (% by wt.) | A 80 |
|---|---|
| 0.20 | 2.6-Dichloro-4-aminophenol |
| 0.25 | Resorcinol |
| Coloration: Glossy gold-brown. | |

EXAMPLE 7

| 0.28 (% by wt.) | A 80 |
|---|---|
| 0.20 | 2.6-Dichloro-4-aminophenol |
| 0.63 | 1-Methyoxy-2-amino-4-(β-hydroxyethyl amino)benzene sulfate |
| Coloration: Glossy deep blue. | |

What is claimed is:

1. Oxidation-based hair dyeing composition for providing, intensive coloration, comprising a combination components of a) 2-(2,5-diaminophenyl)ethanol or water soluble salts thereof, and b) 2,6-dichloro-4-aminophenol.

2. Hair dyeing composition according to claim 1, wherein components a) and b) are present in a weight proportion between 1:5 and 5:1.

3. Hair dyeing composition according to claim 1, further comprising at least one component selected from the group consisting of 1-methoxy-2-amino-4-(β-hydroxyethyl amino)benzene, 2-amino-3-hydroxypyridine, 2,6-diaminopyridine, 3-amino-2-methyl amino-6-methoxypyridine, 2-(dimethyl amino)-5-aminopyridine, 2-(2'-hydroxyethyl amino)-5-aminotoluene, 2,5,6-triamino-4-hydroxypyrimidine, 5-amino-2-methyl phenol, 4-amino-3-methyl phenol, 2,5-diamino pyridine, 2-amino-5-N,N-diethyl aminotoluene, 1,4-diaminobenezene, 2,5-diaminotoluene, 1,3-diaminobenzene, 1-methyl-2-hydroxy-4-aminobenzene, resorcinol, 2-methyl resorcinol, 4-chlororesorcinol, 1-napthol, 2-aminophenol, 3-aminophenol, 5-amino-2-methoxyphenol, 2-amino-4-(β-hydroxyethyl amino)anisole and the water-soluble salts thereof.

4. Hair dyeing composition according to claim 2, further comprising at least one component selected from the group consisting of 1-methoxy-2-amino-4-(β-hydroxyethyl amino)benzene, 2-amino-3-hydroxypyridine, 2,6-diaminopyridine, 3-amino-2-methyl amino-6-methoxypyridine, 2-(dimethyl amino)-5-aminopyridine, 2-(2'-hydroxyethyl amino)-5-aminotoluene, 2,5,6-triamino-4-hydroxypyrimidine, 5-amino-2-methyl phenol, 4-amino-3-methyl phenol, 2,5-diamino pyridine, 2-amino-5-N,N-diethyl aminotoluene, 1,4-diaminobenezene, 2,5-diaminotoluene, 1,3-diaminobenzene, 1-methyl-2-hydroxy-4-aminobenzene, resorcinol, 2-methyl resorcinol, 4-chlororesorcinol, 1-napthol, 2-aminophenol, 3-aminophenol, 5-amino-2-methoxyphenol, 2-amino-4-(β-hydroxyethyl amino)anisole and the water-soluble salts thereof.

\* \* \* \* \*

UNITED STATES PATENT AND TRADEMARK OFFICE
CERTIFICATE OF CORRECTION

PATENT NO.    : 6,224,637 B1
DATED         : May 1, 2001
INVENTOR(S)   : Frank Golinski; Heribert Lorenz; and Rudolf Wagner It is certified that error appears in the above-identified patent and that said Letters Patent is hereby corrected as shown below:

<u>Column 4,</u>
Line 51, delete the "comma" after "providing";
Line 52, "components of" should read -- of components --.

Signed and Sealed this

Sixth Day of November, 2001

Attest:

*Nicholas P. Godici*

NICHOLAS P. GODICI
*Attesting Officer*   *Acting Director of the United States Patent and Trademark Office*